United States Patent [19]
Nicholass et al.

[11] Patent Number: 5,502,218
[45] Date of Patent: Mar. 26, 1996

[54] PROCESS FOR THE PRODUCTION OF KETENE DIMERS

[75] Inventors: John F. Nicholass, Portishead, England; Piotr Zettinger, Huddinge, Sweden

[73] Assignee: Eka Nobel AB, Sweden

[21] Appl. No.: 302,801

[22] PCT Filed: Feb. 14, 1994

[86] PCT No.: PCT/SE94/00118

§ 371 Date: Sep. 15, 1994

§ 102(e) Date: Sep. 15, 1994

[87] PCT Pub. No.: WO94/19306

PCT Pub. Date: Sep. 1, 1994

[30] Foreign Application Priority Data

Feb. 22, 1993 [SE] Sweden ................................ 9300584

[51] Int. Cl.$^6$ .................................................. C07D 305/12
[52] U.S. Cl. ............................................................ 549/329
[58] Field of Search ............................................. 549/329

[56] References Cited

U.S. PATENT DOCUMENTS 5,399,774  3/1995  McIntosh ........................ 549/329

FOREIGN PATENT DOCUMENTS 0550107  7/1993  European Pat. Off. ........ C07C 45/89
3434212  3/1986  Germany ..................... C07D 305/12

OTHER PUBLICATIONS

Derwent Patent Abstract—Abstracting Japanese Patent Publication No. 63/258471, published Oct. 25, 1988.

Patent Abstracts of Japan—Abstracting Japanese Patent Publication No. 63–258471, published Oct. 25, 1988. Vol. 13, No. 63 (C–568).

Primary Examiner—James H. Reamer
Attorney, Agent, or Firm—Ralph J. Mancini; Louis A. Morris

[57] ABSTRACT

A process for the production of ketene dimers from fatty acid halides by reaction with tertiary amines. The process is operated batchwise and the reaction is started in the presence of an initial reaction mixture containing ketene dimer and pre-prepared crystals of tertiary amine hydrogen halide and is carried out in the substantial absence of additional solvents.

18 Claims, No Drawings

PROCESS FOR THE PRODUCTION OF KETENE DIMERS

The present invention relates to a process for the production of ketene dimers from fatty acid halides and tertiary amines and more particularly to a process for the production of ketene dimers according to which the process is operated batchwise and the reaction is started in the presence of an initial reaction mixture containing ketene dimer and pre-prepared crystals of tertiary amine hydrogen halide and is carried out in the substantial absence of additional solvents.

Long-chain "alkyl" ketene dimers (AKD) are extensively used in the papermaking industry as sizing agents and usually in the form of aqueous dispersions comprising cationic starch or cationic synthetic polymers as dispersing agents.

Long-chain alkyl ketene dimers are produced by removal of hydrogen halide from fatty acid halides. The intermediate ketene is highly reactive and dimerizes. Conventionally the production of long-chain alkyl ketene dimers is carried out by addition of a tertiary amine to a fatty acid chloride substrate in an organic solvent, or by addition of fatty acid chloride to a tertiary amine in an organic solvent. The organic solvents which are used are inert with regard to the starting materials and the end-product. The tertiary amine removes hydrogen chloride from the fatty acid chloride and crystals of amine hydrochlorides are formed. These crystals are then removed and the solvent is evaporated.

As inert solvents alkanes, cycloalkanes or aromatic hydrocarbons can be used. Usually aromatic hydrocarbons, such as toluene or 1,2-dichloropropane, are used in commercial processes. The amount of solvent is usually fairly high and most often at least 0.8 parts solvent as to 1 part fatty acid chloride is used. The solvent acts both as a solvent for the fatty acid halide and the AKD and as a diluent to keep the formed crystals apart during the reaction and thereby to prevent growth of the crystals resulting in inclusion of the starting materials and end-products. Such crystal growth with inclusions leads to decreased yield. All work with organic solvents, such as toluene, is of course undesirable from an environmental point of view and requires stringent safety measures. Further, it is extremely difficult to remove all solvent from the produced AKD and this will thus usually contain about 0.1 to 0.6 per cent by weight of solvent, which of course is undesirable and which causes problems at the use of the AKD as a sizing agent. Thus the solvent will be present in the paper produced, effluent from the paper machine and in exhaust from dryers.

Attempts to reduce the amount of inert organic solvents in the production of ketene dimers have not been successful. This is mainly due to the crystal growth and the shape of the formed crystals, which to a certain extent is dependent on the type of solvent. It is also believed that the crystal shape can be influenced in a manner which is negative with regard to viscosity by interactions between free tertiary amine and formed amine salts. In particular, the dendritic growth of the crystals of tertiary amine hydrohalide results in needle-shaped crystals and/or crystals having dendritic side branches, leading to an undesirably high viscosity in the reaction mixture. Thus it becomes very difficult to stir the reactor contents and heat transfer problems arises. In addition, such crystal growth occuring in the presence of a minor amount of inert organic solvent usually leads to inclusions and substantially decreased purity of the ketene dimer.

The present invention aims at providing a process for the production of ketent dimers from fatty acid halides and tertiary amines whereby the problems connected with the use of inert organic solvents can be avoided. This is achieved by providing a process as defined in the claims. More specifically, the present invention relates to a process for the production of ketene dimers from fatty acid halides and tertiary amines wherein the process is operated batchwise and the reaction is started in the presence of an initial reaction mixture containing ketene dimer and pre-prepared crystals of tertiary amine hydrogen halide and is carried out in the substantial absence of additional solvents.

The present invention makes it possible to produce ketene dimers from fatty acid halides and tertiary amines in a very advantageous manner by the presence of ketene dimer and pre-prepared crystals of tertiary amine hydrogen halide in the starting stage of the reaction. As ketene dimer and crystals of tertiary amine hydrogen halide are formed in the present reaction, the initial reaction mixture is preferably a so-called heel of pre-prepared reaction mixture containing ketene dimer and crystals of tertiary amine hydrogen halide. According to the invention it has been found that the shape of the crystals formed at the present reaction conditions are essentially different from the shape of the crystals formed in conventional solvent based processes. It is believed that the crystal growth at the present reaction conditions mainly takes place in the form of substantially hexagonal prismatic crystals and that such crystals act as nucleating agents for further crystal growth. Hereby it is possible to prevent or to a great extent reduce the dendritic growth leading to formation of dendritic, needle-shaped crystals and crystals having dendritic side branches. Thus, the pre-produced tertiary amine salt crystals present at the starting stage of the present reaction provide favourable crystallization and crystal growth conditions for the new crystals that will be formed in the reaction. As a result, the viscosity of the reaction mixture will be sufficiently low to make it possible to start the reaction in the initial reaction mixture containing ketene dimer and pre-prepared crystals of tertiary amine hydrohalide as a single reaction medium.

The present process is thus advantageous in that it can be operated in the absence or substantial absence of additional solvents, such as toluene, which makes it possible to avoid all environmental and health problems connected with the solvent use and also means that a solvent removal step in the process can be dispensed with. By substantial absence of additional solvents is meant that not more than 10% by weight, based on the amount of fatty acid halide, of materials which act as solvents/diluents and which are inert with regard to the starting materials and the end-product, such as toluene etc., are present during the process. If additional solvents are present in amounts higher than 10% the produced AKD will probably be disadvantageous in that it will contain too much solvent. Up to this limit the present process will, however, give productivity advantages in comparison with known solvent based processes. Suitably not more than 5% by weight, and preferably not more than 2% by weight, of additional solvent, based on the fatty acid halide, is used in the process. It is of course a great advantage of the present process that it is possible to entirely avoid the use of additional solvents.

The process is further advantageous since it can be operated with a very minor excess of tertiary amine which means that negative influence of this on formed tertiary amine salt crystals can be reduced and that work-up of the produced AKD is simplified. Thus, besides the great environmental advantages, the present invention also provides a technically as well as economically advantageous process for the production of ketene dimers.

The starting material for the present process is a fatty acid halide which can have up to 30 carbon atoms, suitably with from 12 to 22 carbon atoms and preferably with from 16 to 18 carbon atoms, or a mixture of such fatty acid halides. The fatty acid halide can be a halide of a saturated or unsaturated fatty acid and as some examples can be mentioned halides of lauric acid, myristic acid, palmitic acid, stearic acid, arachidic acid, palmitoleic acid, oleic acid etc. Halides of naturally occurring fatty acids such as those from coco and tallow can of course also be used. The fatty acid halide is usually a chloride and stearic acid chloride is of particular technical interest.

The tertiary amine used in the present process can be a monoamine or diamine. The tertiary amine should be liquid at the reaction conditions. The tertiary amine is suitably a monoamine of the formula $R_1R_2R_3N$, wherein $R_1$, $R_2$ and $R_3$ independent of each other can be alkyl, alkenyl, aralkyl such as benzyl, or cycloalkyl groups having from 1 to 10 carbon atoms, or $R_1$ and $R_2$ together can form an alkylene chain having up to 6, preferably 4 to 5 carbon atoms, whereby the amines are selected so that the total number of carbon atoms give an amine which is liquid at the reaction conditions. Aliphatic amines are preferred and they preferably have from 1 to 6 carbon atoms in each R group. Suitable amines can be selected from triethylamine, diethylmethylamine, dimethylcyclohexylamine, di-isopropylethylamine, tripropylamine, N-methylpyrrolidine and N-methylpiperidine. The use of blends of two or more amines is, of course, also within the scope of the invention. Triethylamine (TEA) is the preferred tertiary amine, mainly for its physical properties and for economic reasons.

An advantage of the present process is that it does not require high amounts of tertiary amine which means that negative influence on crystal shapes from excess of this can be avoided and which also simplifies work-up. The amount of tertiary amine should correspond at least to the stoichiometric amount and usually at least 1.05 moles of tertiary amine are used for each mole of fatty acid halide. The upper limit is first of all dependent on economic considerations and suitably the amount of amine does not exceed 1.5 moles per mole of fatty acid halide and preferably it does not exceed 1.4 moles.

In the present process the reaction between the fatty acid halide and the tertiary amine can be started in the presence of an initial reaction mixture containing ketene dimer and pre-prepared crystals of tertiary amine hydrogen halide. The initial reaction mixture can be prepared by simply adding tertiary amine hydrohalide crystals prepared in known manner to ketene dimer or to a mixture containing ketene dimer or by purging hydrogen halide gas through a mixture containing ketene dimer and tertiary amine. Further, the initial reaction mixture can be obtained by the reaction of a fatty acid halide and a tertiary amine. In addition to ketene dimer and crystals of tertiary amine hydrogen halide, the initial reaction mixture can contain minor amounts of reaction-typical impurities and by-products such as fatty acids and fatty acid anhydrides as well as any unreacted starting materials such as tertiary amine.

The initial reaction mixture contains pre-prepared crystals of tertiary amine hydrohalide in an amount sufficient for the crystals therein to fulfil their function as nucleating agents for further growth of crystals providing a reaction mixture having advantageous viscosity properties, and the amount should be at least 1% by weight. The upper limit of the amount of crystals in the initial reaction mixture depends on the crystal shapes and the equipment used. It can be 50% by weight or even higher, as long as it is possible for the initial reaction mixture to function as a reaction medium during the initial reaction stage. However, the initial reaction mixture contains crystals of tertiary amine hydrohalide preferably in an amount of from 20 to 45% and most preferably in an amount of from 30 to 40% by weight of the initial reaction mixture. The pre-prepared crystals of tertiary amine hydrohalide in the initial reaction mixture may be a mixture of different tertiary amine hydrohalides and/or a mixture of different shaped crystals.

The initial reaction mixture, and in particular the AKD present therein, will to a certain extent function as a solvent/diluent or as a reaction medium for the reaction and it is hereby possible to entirely dispense with additional solvents/diluents, such as toluene etc., which are used in conventional AKD processes. Although it is a great advantage that additional solvents are not required in the present process, it is of course possible to include an additional solvent in the present process and small amounts of additional solvents might be advantageous depending on the acid halide.

The amount of initial reaction mixture for the initial reaction stage should be sufficient for it to function as a reaction medium during this stage. The amount or volume of the initial reaction mixture necessary for this can easily be determined by the man skilled in the art with regard to the design of the specific reactor which is used and with regard to reaction rate etc., since of course once the reaction has started formed reaction mixture product will act as a reaction medium. The weight ratio of the initial reaction mixture to the fatty acid halide to be used in the reaction can be within the range of from 3:1 to 1:30, suitably in the range 1:1 to 1:15 and preferably in the range 1:3 to 1:8.

In a preferred embodiment of the present invention the reaction is started in the presence of a so-called heel of pre-prepared reaction mixture containing ketene dimer and crystals of tertiary amine hydrohalide. It has been found that a heel for several consecutive runs can be made up from the reaction mixture containing ketene dimer and tertiary amine hydrohalide crystals from an earlier run without loss in product quality. A portion of the batch is hereby suitably retained in the reactor as a heel for the next batch. It is thus obvious that the present process offers the possibility of very satisfactory utilization of reaction equipment, especially since high amounts of inert diluents can be avoided. Use is suitably made of a heel containing ketene dimer and crystals of tertiary amine hydrohalide in proportions which are substantially stoichiometric with regard to ketene and crystals.

In the present process the tertiary amine can be added to a fatty acid halide present in the initial reaction mixture, or by addition of the fatty acid halide to a tertiary amine present in the initial reaction mixture. Of these two types of charging orders it is preferred to charge the tertiary amine to the initial reaction mixture first and then charge the fatty acid halide.

According to a particularly preferred embodiment of the present invention the two reactants, i.e. the fatty acid halide and the tertiary amine, are charged in a parallel manner, i.e. they are charged separately and simultaneously. This method of addition has been found to give the best working conditions with regard to viscosity of the reaction mixture etc.. Preferably the reactants are charged and mixed in the pre-prepared reaction mixture whereby the reaction takes place in the presence of an excess of ketene dimer and tertiary amine hydrohalide crystals.

The following will illustrate suitable conditions for the preferred process according to the invention for the production of AKD from hardened tallow fatty acid chloride and triethylamine. Suitable conditions for other fatty acid halides and other tertiary amines are easily determined by the man skilled in the art taking into consideration the melting points of the fatty acid halide and of the produced AKD, respectively, and the physical properties of the tertiary amine. The process is suitably carried out by first heating the initial reaction mixture containing AKD and pre-prepared tertiary amine salt crystals to a temperature of at least 50° C. in order to get the AKD in the mixture in a molten state. The tertiary amine and the fatty acid halide are then added in a parallel mode, i.e. they are added separately but simultaneously, and the tertiary amine and the fatty acid halide are preferably charged sub-surface with regard to the surface of the initial reaction mixture and the surface of the formed reaction mixture. Alternatively, the tertiary amine is suitably charged supra-surface, while the fatty acid halide most suitably is charged sub-surface.

The rates of addition of the respective reactants can vary and be adjusted along the reaction. It has been found that it is important that the rates of addition should not be too high with respect to the amount of reaction mixture in the reactor. Too rapid addition of the reactants to the reaction mixture results in the formation of much smaller crystals of tertiary amine hydrohalide and much higher viscosity of the reaction mixture, which is very undesirable. Preferably the rate of addition, expressed as total moles of reactants per mole of AKD in the reaction mixture per hour, should be less than 8, most preferably less than 4. Obviously another factor which dictates the permissible rate of addition is the that heat can be removed from the reactor. Usually the additions take from 1.5 to 4 hours and the reaction is usually carried out at a temperature of from 50° to 65° C. and especially at 55° to 60° C., and the temperature is dependent on the boiling point/melting point of the tertiary amine and fatty acid halide, respectively. The reaction between the fatty acid halide and the tertiary amine is exothermic and the reaction is thus usually carried out under cooling. After finished additions the reaction mixture is usually post-reacted for a period of up to 2.5 hours as is conventional. The temperature during the post-reaction is suitably kept within the range of from 60° to 85° C.

After completed reaction the produced AKD is separated from the formed crystals of tertiary amine hydrogen halide and worked-up in a conventional manner. A part of the produced reaction mixture containing AKD and crystals of tertiary amine hydrogen halide is suitably left in the reactor to serve as a heel for direct consecutive run and the work-up be carried out in a separate vessel. To separate the amine hydrohalide crystals from the AKD an acid extraction step is used as is conventional and is carried out by addition of inorganic acid, such as hydrochloric acid or sulphuric acid, suitably hydrochloric acid. The extraction step is suitably carried out under stirring and at a temperature of from about 60° C. to about 80° C. The concentration of acid is dependent on the amount of amine remaining in the slurry. Calculations are based on an excess of acid at a concentration to produce a triethylamine salt solution of from 40 to 60% by weight water. The aqueous phase formed in the acid extraction step is separated from the AKD.

The AKD can be worked up in per se conventional manner and usually a water wash is carried out to remove impurities followed by a dehydration step to remove remaining water. For AKD produced from hardened tallow fatty acid chloride and triethylamine the water wash is suitably carried out at a temperature of from 50° to 90° C. under stirring. A dehydration step usually involves heating to temperatures of from about 70° to about 90° C. under vacuum for about 30 minutes to about 1 hour. Suitable conditions for AKD from other fatty acid halides and other tertiary amines are easily determined by the man skilled in the art. If desired, depending on the purity requirements in the intended use of the AKD, a filtration step can be carried out as a last step in order to remove any minor amounts of tertiary amine hydrogen halide and solid residues that may remain.

The AKD produced according to the present process is of good quality and in addition it can be entirely solvent-free and does then not cause any problems when used as sizing agent. In this field it can be used as conventionally in aqueous dispersions which can contain anionic, cationic or amphoteric dispersing agents or protective colloids. Usually AKD dispersions contain anionic dispersion agents, such as lignosulphonates or sodium salts of condensed aromatic sulphonic acids, and cationic polymers, for example cationic starch or cationic synthetic polymers such as polyacrylamide, polyamines etc.

The aqueous phase obtained after the acid extraction step described above will have to be worked up in order for the tertiary amine to be re-used. Such a work-up will, as conventionally, involve neutralisation with alkali, suitably caustic soda, to liberate free amine from the hydrogen chloride salt. Any small amounts of water in the free amine are then suitably removed to bring the water content down to less than 1200 ppm, preferably less than 200 ppm before reuse. Dehydration of the amine can for example be carried out by fractional distillation, chemical treatment, e.g. with calcium hydride or molecular sieves, or a combination thereof.

The invention is further illustrated in the following examples which, however, are not intended to limit the same. Parts and per cent relate to parts by weight and per cent by weight, respectively, unless otherwise stated.

The equipment used in the examples was as follows: The reaction vessel consisted of a one liter jacketed reaction vessel fitted with a bottom outlet tap of 3.5 mm diameter. The vessel was fitted with a stirrer, a condenser, a thermometer reading from −5° to +105° C. at 0.5° C. intervals and a dry nitrogen purge. The reaction vessel was also fitted with two subsurface reactant inlet tubes connected to Masterflex™ peristaltic pumps fitted with No. 13 Viton tubing. These pumps were fed from reactant reservoirs placed on electronic balances to give continuously monitored addition quantities. The inlet tubes reached just above the stirrer. In Examples 2–4, one of the reactant inlet tubes was replaced with a graduated addition funnel (balanced) for suprasurface addition of the tertiary amine. The jacket was filled with hot water circulated from an external bath. A separate, identical jacketed one liter reaction vessel, fitted with thermometer, stirrer, condenser and vacuum system was employed as a washing vessel for washing and dehydration of the reaction products. The jacket was filled with hot water circulated from an external bath.

EXAMPLE 1

In this example an initial reaction mixture was prepared by charging 69.4 g of molten AKD (prepared from hardened tallow fatty acid chloride), 35.3 g of triethylamine hydrochloride crystals, prepared in known manner from triethylamine and hydrochloric acid, and 2.05 g of triethylamine to the reaction vessel. The reaction mixture was stirred at 60° C. for 30 minutes under dry nitrogen.

To the fatty acid chloride reservoir was charged 437.5 g (1.5 moles) of hardened tallow fatty acid chloride and to the amine reservoir was charged 163.3 g (1.62 moles) of triethylamine. Simultaneous sub-surface additions of the reactants were commenced, the fatty acid chloride at 2.18 g/min and triethylamine at 0.81 g/min, keeping the temperature at 58°–60° C. During addition the viscosity remained low throughout the addition (less than 200 cps). At the end of the addition a small sample of the slurry was removed and the wax components removed from the crystals by gentle washing with toluene and diethyl ether. The crystals were examined under a microscope and seen to be mainly hexagonal prismatic crystals with a typical size in the range of 10–35 μm. Some much larger crystals were seen and were thought to have originated from the initial charge of triethylamine hydrochloride.

The reaction mixture was stirred for 1 hour at 60° C. after the addition. During this period 184.0 g of water and 39.0 g of 30% hydrochloric acid was charged to the washing vessel and heated to 75° C. A volume of reaction slurry equivalent to the reactants charged was transferred to the washing vessel over 10 minutes leaving a heel of reaction mixture in the reaction vessel. The mixture in the washing vessel was heated to 72° C. and stirred for 10 minutes. The stirring was stopped and the phases allowed to separate. 425 g of triethylamine hydrochloride solution was removed and a further 69.6 g of hot water charged to the washing vessel. The mixture was gently stirred and heated to 75° C. then allowed to separate for 30 minutes. The aqueous layer (66.2 g) was removed and the molten AKD dehydrated at 75° C. under vacuum with a purge of nitrogen gas. The molten AKD was run out to give a wax with an AKD content of 82.6% and residual fatty acid content of 2.0%.

EXAMPLE 2

In this example use was made of a heel which was previously prepared in a similar manner to Example 1. The present reaction was carried out immediately after the previous reaction leaving the molten heel in the reaction vessel. The heel had a calculated weight of 150.3 g and contained (estimated) 67.8% of AKD wax (as in Example 1), 29.0% of triethylamine hydrochloride and 3.2% of triethylamine.

The molten heel was cooled to 55° C. with stirring and the sub-surface addition of 436.5 g (1.50 moles) of hardened tallow fatty acid chloride was commenced with stirring. Simultaneously supra-surface addition of 174.3 g (1.72 moles) of triethylamine was started from a gas balanced addition funnel. The addition rates were 3.41 g/min for fatty acid chloride and 1.26 g/min for triethylamine. The temperature of the reaction mixture was held at 52°–55° C. by adjusting the temperature of the circulating jacket water.

During the additions of acid chloride and triethylamine the viscosity of the mixture was observed to increase. However, the mixture was still stirring freely. After the additions were completed the mixture was heated to 70° C. over 15 minutes, then held at 70°–72° C. for 2 hrs. During this time interval 227.25 g of water and 62.7 g of concentrated hydrochloric acid were charged to the washing vessel and heated to 70° C. The acid wash was run out into a 2 liter beaker and weighed.

582.9 g of the reaction slurry was run out from the reactor base valve into the wash with gentle stirring, leaving a heel of reaction mixture in the reaction vessel. The two phase mixture in the beaker was recharged to the washing vessel, reheated to 70° C. with stirring and the stirrer stopped. The layers were allowed to separate for 30 minutes, the lower phase was separated to give 462.7 g of triethylamine hydrochloride solution. A further 227 g of water were charged to the washing vessel and the mixture gently stirred and reheated to 75° C. The layers were allowed to separate for 30 minutes and the aqueous phase separated. The organic phase (404.0 g) was dehydrated at 80° C. at 1.0 mm Hg pressure to give 401.1 g of yellow oil. This solidified to pale yellow solid wax. The purity of the product was 82.5% as assayed by IR.

EXAMPLE 3

This reaction was carried out 3 days after the end of Example 2. The estimated quantity of heel left in the reaction vessel was 173.2 g. The heel contained (estimated) 63.6% of AKD wax, 32.7% of triethylamine hydrochloride and 3.7% of triethylamine.

The solidified heel remaining from Example 2 was reheated to melt and sampled. The temperature was adjusted to 55° C. with stirring. Supra-surface addition of 174.3 g (1.72 moles) of triethylamine and sub-surface addition of 436.5 g (1.50 moles) of hardened tallow fatty acid chloride were started. The addition rate of fatty acid chloride was 4.16 g/minute, for triethylamine the addition rate was 1.52 g/minute. The temperature was controlled at 52°–55° C. during the addition by adjusting the temperatures of the circulating water. After the addition was complete the reaction mixture was heated to 70° C. over 15 minutes. It was held at 70°–72° C. for 2 hours. 592.4 g of reaction mixture was then worked up as in Example 2 to give 467.1 g of triethylamine hydrochloride solution, 386.8 g of wet reaction product resulting in 382.5 g of dehydrated final product having a purity of 85.5%.

EXAMPLE 4

A molten heel, weighting 61.3 g and containing (estimated) 60.9% of AKD wax (as in Example 1), 36.8% of crystals of tripropylamine hydrochloride and 2.3% of tripropylamine, was present in the reaction vessel from a previous reaction. The heel was prepared in a similar manner to Example 1, but with the difference that tripropylamine was used instead of triethylamine.

211.0 g (1.47 moles) of tripropylamine were charged to the addition funnel and 399.0 g (1.37 moles) of hardened tallow fatty acid chloride were charged to the reservoir. The reactants were continuously added supra-surface and sub-surface, respectively, over 2½ hours keeping the reactor temperature at 60°±2° C. After the addition the reaction mixture was heated to 70° C. for 60 minutes, then 280 g of 6.0% hydrochloric acid was added and the mixture stirred and heated to 70° C. The mixture was stirred at 70° C. for 10 min, allowed to separate for 20 min, then the bottom layer run off to give 527.8 g of aqueous phase. The molten organic layer was washed with 100 g of water at 75° C. for 5 min, allowed to separate for 30 minutes, then the hazy lower layer removed. The molten product was dehydrated under vacuum (15 mm Hg) with a nitrogen purge to give 381.0 g of clear yellow oil which solidified to a wax on cooling. The purity of the AKD wax was 50.1% (IR).

EXAMPLE 5

A molten heel, weighting 51.0 g and containing (estimated) 70.2% of AKD wax (as in Example 1), 28.2% of crystals of diethylmethylamine hydrochloride and 1.6% of diethylmethylamine, was remaining in the reaction vessel from a previous reaction. The heel was prepared in a similar manner to Example 1, but with the difference that diethylmethylamine was used.

112.9 g (1.29 moles) of diethylmethylamine (water content 600 ppm) and 349.4 g (1.20 moles) of hardened tallow fatty acid chloride were charged to the reservoirs. The reactants were continuously added sub-surface over 2.5 hours keeping the reactor temperature at 56°±1° C. After the addition the relatively viscous reaction mixture was heated to 65° C. for 30 min, then transferred with nitrogen pressure to the washing vessel containing 217 g of 3.0% hydrochloric acid heated to 75° C. The mixture was stirred at 75° C. for 10 min, allowed to separate for 20 min, then the bottom layer run off to give 365.8 of aqueous phase. The molten organic layer was worked up as in Example 4 to give 323.8 of clear yellow oil which solidified to wax on cooling. The wax had an AKD content of 88.8%, as assayed by IR, and a content of free fatty acid of 6.3%, as assayed by gas chromathography (GC).

EXAMPLE 6

A molten heel, weighting 53.3 g and containing (estimated) 74.2% of AKD wax (as in Example 2), 24.4% of crystals of isopropyl dimethylamine hydrochloride and 1.4% of isopropyl dimethylamine, was present in the reaction vessel from a previous reaction. The heel was prepared in a similar manner to Example 1, but with the difference that isopropyldimethylamine was used.

The reactants, 246.2 g (0.84 moles) of hardened tallow fatty acid chloride and 79.7 g (0.91 moles) of isopropyldimethylamine (water content 300 ppm) were added in a similar manner to Example 5. The mixture was post-reacted as in Example 5. 123.7 g of 5% of hydrochloric acid was added with stirring. The mixture was stirred at 75° C. for 10 min, transfered to the washing vessel, allowed to separate for 20 min, then the bottom aqueous phase run off. The molten organic layer was worked up as in Example 4 and further filtered hot to give 239.3 g of clear yellow oil which solidified to a wax on cooling. The wax had a content of AKD of 88.5% (IR) and a content of free fatty acid of 4.3% (GC).

EXAMPLE 7

A molten heel, weighting 119.6 g and containing (estimated) 60.7% of AKD wax (as in Example 1), 36.8% of crystals of di-isopropylethylamine hydrochloride and 2.5% of di-isopropylethylamine, was present in the reaction vessel from a previous reaction. The heel was prepared in a similar manner to Example 1, but with the difference that di-isopropylethylamine was used.

The reactants, 227.1 g (0.78 moles) of hardened tallow fatty acid chloride and 109.5 g (0.85 moles) of diisopropylethylamine (water content 300 ppm) were continuously added sub-surface over 2.75 hours keeping the reactor temperature at 60°±1° C. After the addition the relatively viscous reaction mixture was heated to 65° C. for 30 min, then transferred with nitrogen pressure to the washing vessel containing 182 g of 5.0% hydrochloric acid heated to 70° C. The mixture was stirred at 75° C. for 10 min, allowed to separate for 20 min, then the bottom layer run off to give 360.0 g of aqueous phase. The molten organic layer was worked up as in Example 5 to give 289.4 g of clear yellow oil which solidified to wax on cooling. The purity of the AKD wax was 21.5%.

We claim:

1. A process for the production of ketene dimers which comprises reacting fatty acid halides with tertiary amines, wherein the process is operated batchwise and the reaction is started in the presence of an initial reaction mixture containing ketene dimer and pre-prepared crystals of tertiary amine hydrogen halide and said process is carried out in the substantial absence of additional solvents.

2. The process of claim 1, wherein the reaction is started in the presence of an initial reaction mixture obtained by the reaction of a fatty acid halide and a tertiary amine containing ketene dimer.

3. The process of claim 1 wherein the initial reaction mixture comprises crystals of tertiary amine hydrogen halide in an amount of from 1 to 50% by weight.

4. The process of claim 1, wherein the weight ratio of the initial reaction mixture to the fatty acid halide is within the range of from 3:1 to 1:30.

5. The process of claim 1, wherein the fatty acid halide and the tertiary amine are charged in a parallel manner.

6. The process of claim 1 wherein at least 1.05 moles of tertiary amine are used per mole of fatty acids halide.

7. The process of claim 1 wherein the tertiary amine is an amine of formula $R_1R_2R_3N$ wherein $R_1$, $R_2$ and $R_3$ independent of each other are alkyl groups or cycloalkyl groups having from 1 to 10 carbon atoms, or $R_1$ and $R_2$ together form an alkylene chain having up to 6 carbon atoms.

8. The process of claim 7, wherein the tertiary amine is selected from triethylamine, diethylmethylamine, dimethylcyclohexylamine, di-isopropylethylamine, tripropylamine, N-methyl pyrrolidine, N-methylpiperdine and mixtures thereof.

9. The process of claim 1, wherein the fatty acid halide is a chloride of a saturated or unsaturated fatty acid having from 12 to 22 carbon atoms.

10. The process of claim 1 wherein the reaction is carried out in the absence of additional solvents.

11. The process of claim 2 wherein the initial reaction mixture comprises crystals of tertiary amine hydrogen halide in an amount of from 1 to 50% by weight.

12. The process of claim 5 wherein at least 1.05 moles of tertiary amine are used per mole of fatty acid halide.

13. The process of claim 1, wherein the reaction is carried out in the presence of not more than 10% by weight, based on the amount of fatty acid halide, of additional solvents.

14. The process of claim 13, wherein the reaction is carried out in the presence of not more than 5% by weight, based on the amount of fatty acid halide, of additional solvents.

15. The process of claim 1, wherein the additional solvents are inert solvents.

16. The process of claim 13, wherein the additional solvents are inert solvents.

17. The process of claim 14, wherein the additional solvents are inert solvents.

18. The process of claim 9, wherein the fatty acid halide is a chloride of a saturated or unsaturated fatty acid having from 16 to 18 carbon atoms.

* * * * *